US00PP09344P

United States Patent [19]

Zary

[11] Patent Number: Plant 9,344

[45] Date of Patent: Oct. 31, 1995

[54] HYBRID TEA ROSE PLANT NAMED 'JACDEEP'

[75] Inventor: Keith W. Zary, Thousand Oaks, Calif.

[73] Assignee: Bear Creek Gardens, Inc., Medford, Oreg.

[21] Appl. No.: 316,864

[22] Filed: Oct. 3, 1994

[51] Int. Cl.[6] ..... A01H 5/00

[52] U.S. Cl. ..... Plt./20

[58] Field of Search ..... Plt./19, 20, 21

*Primary Examiner*—Howard J. Locker

*Attorney, Agent, or Firm*—Klarquist Sparkman Campbell Leigh & Whinston

[57] ABSTRACT

A Hybrid Tea rose plant having deep rose-pink flower color, large flower size, long, strong stems, good cut-flower production and vigorous, upright growth habit.

1 Drawing Sheet

The present invention relates to a new and distinct variety of rose plant of the Hybrid Tea class which was originated by me by crossing the variety KORenlo, U.S. Plant Pat. No. 5,679, with the variety JACreb, unpatented.

The primary objective of this breeding was to produce a new rose variety having the excellent production and vase life of the female parent, combined with the long, strong stems and large flower size of the male parent. These objectives were substantially achieved, along with other desirable improvements, as evidenced by the following unique combination of characteristics that are outstanding in the new variety and that distinguish it from its parents, as well as from all other varieties of which I am aware:

1. Deep rose-pink flower color;
2. Large flower size;
3. Long, strong stems; and
4. Good flower production—180 to 190 stems per square meter.

Asexual reproduction of this new variety by budding, as performed at Wasco, Calif., shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with the Royal Horticultural Society (London) Colour Chart, except where ordinary dictionary significance of color is indicated.

Parentage:

*Seed parent.*—KORenlo.

*Pollen parent.*—JACreb.

Classification:

*Botanical.*—*Rosa hybrida.*

*Commercial.*—Hybrid Tea.

FLOWER

Observations made from specimens grown in a greenhouse environment at Somis, Calif., from January to June 1994.

Blooming habit: Continuous.

Bud:

*Size.*—1¾ inches long when the petals start to unfurl.

*Form.*—The bud form is long, pointed ovoid.

*Color.*—When sepals first divide, bud color is Red Group 46D. When half blown, the upper sides of the petals are Red Group 46D; and the lower sides of the petals are Red Group 46D.

*Sepals.*—Color: Green Group 138C edged in Green Group 138B. Surface texture: Covered in fine hairs. There are three usually normally appendaged sepals with an occasional heavily appendaged sepal. There are two unappendaged sepals with hairy edges.

*Receptacle.*—Color: Green Group 139B. Shape: Funnel. Size: Large (½ inch to ⅝ inch long). Surface: Smooth.

*Peduncle.*—Length: Long (3½ inches to 4 inches). Surface: Smooth, with some small glands. Color: Medium green. Strength: Stiff, erect.

Bloom:

*Size.*—Large. Average open size is 5 inches.

*Borne.*—Singly.

*Stems.*—Long, strong. Average length is about 24 inches to 28 inches.

*Form.*—When first open: High centered. Permanence: Retains its form to the end, outer petals curl back, quill fashion.

*Petalage.*—Number of petals under normal conditions: 30 to 35.

*Color.*—The upper side of the petals is Red Group 46D. The reverse side of the petals is Red Group 46D. The base of each petal has a small, greenish-white half moon at the point of attachment. The major color on the upper side is Red Group 46D.

*Variegations.*—Occasional white streak on the guard petals.

*Discoloration.*—The general tonality at the end of the first day: No change. At the end of the third day, no change, nor any change at the end of the seventh day.

*Fragrance.*—Slight.

Petals:

*Texture.*—Thick.

*Shape.*—Round.

*Form.*—Tips slightly recurved, edges slightly quilled.

*Arrangement.*—Imbricated, with a few petaloids in the center.

*Persistence.*—Drop off cleanly.

*Lastingness.*—On the plant: Long (7 to 8 days). As a cut flower: Long (8 to 10 days).

Reproductive parts:

*Anthers.*—Size: Large. Quantity: Many. Color: Yellow. Arrangement: Regular around styles.

*Filaments.*—Color: Yellow.

*Pollen.*—Color: Gold yellow.

*Styles.*—Color: Red.

*Stigmas.*—Color: Greenish white.

Form: Bush.

Growth: Vigorous, upright, branching, at one year of age a greenhouse plant is 6 to 7 feet tall and 4 feet wide.

Foliage:

*Number of leaflets on normal mid-stem leaves.*—5.

*Size.*—5 to 5½ inches×4 inches.

*Quantity.*—Abundant.

*Color.*—New foliage: Greyed Purple 183D. Old foliage: Green Group 136B on the upper side, Green Group 136C on the lower side.

Leaflets:

*Shape.*—Pointed oval.

*Texture.*—Upper side: Smooth.

*Edge.*—Serrated.

*Serration.*—Single, small.

*Petiole rachis.*—Color: Green.

*Petiole underside.*—Smooth, with an occasional prickle.

*Stipules.*—Short, serrated, bearded.

*Disease resistance.*—Susceptible to mildew under normal growing conditions at Somis, Calif.

Wood:

*New wood.*—Color: Light green. Bark: Smooth.

*Old wood.*—Color: Green. Bark: Smooth.

Prickles:

*Quantity.*—On main canes from base: Ordinary. On laterals from main canes: Ordinary.

*Form.*—Medium (⅜ inch long), hooked downward.

*Color when young.*—Red.

Small prickles:

*Quantity.*—On main stalks: None. On laterals: None.

I claim:

1. A new and distinct variety of rose plant of the Hybrid Tea class, substantially as herein shown and described, characterized particularly as to novelty by the unique combination of its deep rose-pink flower color, large flower size, long, strong stems, good cut-flower production and its vigorous, upright growth habit.

* * * * *

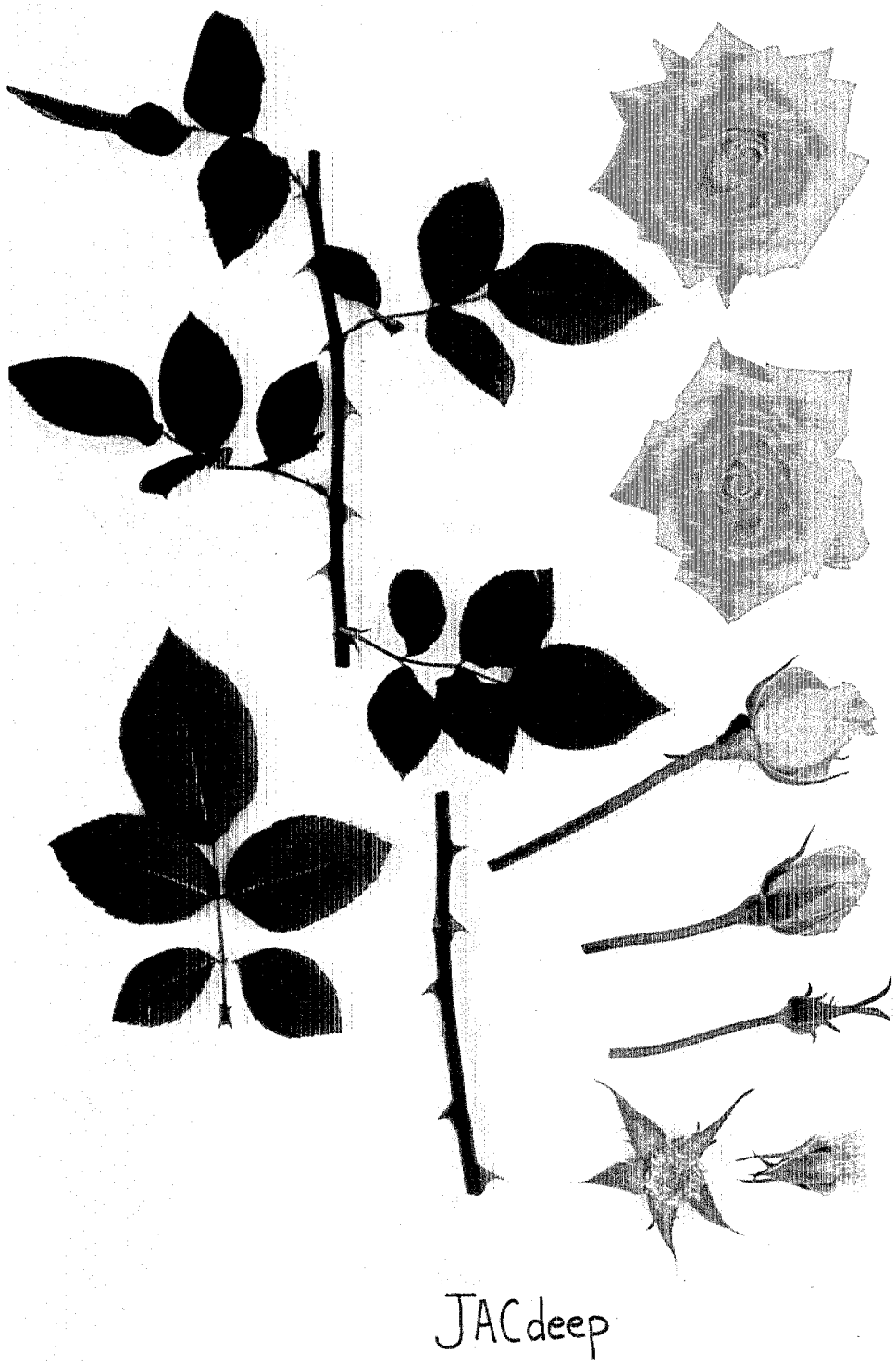
JACdeep